United States Patent

Caubere et al.

[11] Patent Number: 5,491,163
[45] Date of Patent: Feb. 13, 1996

[54] (THIA)CYCLOALKYL[B]INDOLES

[75] Inventors: Paul Caubere, Nancy; Brigitte Jamart-Gregoire, Vandoeuvre les Nancy; Catherine Caubere, Nancy; Jean-Guy Bizot-Espiard, Paris; Pierre Renard, Versailles; Gérard Adam, Le Mesnil le Roi, all of France

[73] Assignee: Adir et Compagnie, Courbevoie, France

[21] Appl. No.: 276,917

[22] Filed: Jul. 19, 1994

[30] Foreign Application Priority Data

Jul. 20, 1993 [FR] France ................................. 93 08862
May 19, 1994 [FR] France ................................. 94 06098

[51] Int. Cl.$^6$ .......................... A61K 31/40; C07D 513/04
[52] U.S. Cl. ........................ 514/411; 548/432; 548/439
[58] Field of Search ........................... 514/411; 548/432, 548/439

[56] References Cited

U.S. PATENT DOCUMENTS 3,329,517  7/1967  Rice et al. ............................ 548/439
3,772,325  11/1973 Epstein et al. ....................... 548/439
3,824,234  7/1974  Epstein .
3,862,953  1/1975  LeBerger .

FOREIGN PATENT DOCUMENTS 0035259  9/1981  European Pat. Off. .
2100677  3/1972  France .
1511169  5/1978  United Kingdom .
0404536  12/1990 United Kingdom .
0409410  1/1991  United Kingdom .

Primary Examiner—Jacqueline Haley
Attorney, Agent, or Firm—Gordon W. Hueschen

[57] ABSTRACT

The invention relates to a compound selected from those of formula (I):

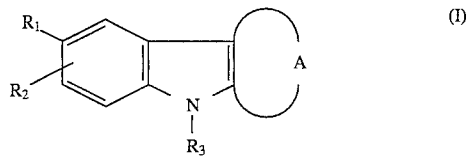

in which $R_1$, $R_2$, $R_3$ and A are as defined in the description, and medicinal product containing the same in order to treat a mammal afflicted with a peroxydation phenomenom.

15 Claims, No Drawings

(THIA)CYCLOALKYL[ B] INDOLES

The present invention relates to (thia)cycloalkyl[b]indoles, to the process for preparing them and to the pharmaceutical compositions containing them.

Some cyclohept[b]indol-6-ones are described in U.S. Pat. No. 3,824,234 as antifungal agents and analgesics.

It is now well established that lipid peroxidation is a major pathological factor. In particular, it is clear that the lipid peroxidation process and the products to which it gives rise can be detrimental to cell viability.

The effects of lipid peroxidation have been involved in many pathological conditions such as atherosclerosis, hemolytic anemias and damage due to ischemia—reperfusion (Oxidative Damage and Repair, Chemical, Biological and Medical Aspects. 1991 Pergamon Press, page xxi). The possibility of having available molecules which make it possible to combat this lipid peroxidation phenomenon is therefore found to be of great use to the clinician for the prevention and the treatment of pathology involving such a phenomenon.

The Applicant Company has found new (thia)cycloalkyl [b]indoles which have a powerful antioxidant effect and allow lipids, and especially human LDLs (low density lipoproteins) to be protected against oxidation.

The invention relates more particularly to the compounds of formula (I):

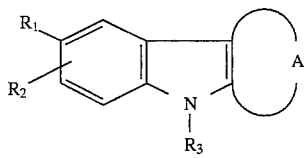

in which:

A denotes an alkylene chain —(CH$_2$)m— with m denoting 5 or 6 or a group of formula (a)

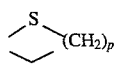

in which p is between 1 and 4,

R$_1$ denotes a radical chosen from:
hydroxyl,
thiol,
—O—R$_4$ with R$_4$ being chosen from alkyl and acyl;
and —S—R$_5$ with R$_5$ being chosen from alkyl, phenyl and benzyl;
R$_2$ denotes a radical chosen from hydrogen, halogen, alkyl, alkoxy and trifluoromethyl;
R$_3$ denotes a radical chosen from alkyl, acyl, carboxyalkyl and alkoxycarbonylalkyl; and, in the case where A is other than a pentamethylene, R$_3$ may also denote a hydrogen, provided that if m denotes 5, R$_2$ denotes a hydrogen and R$_1$ denotes a methoxy, while R$_3$ cannot denote a methyl, their optical isomers, in pure form or in mixed form, when R$_1$, R$_2$ or R$_3$ have a chiral center,
and their salts of addition to a pharmaceutically acceptable base, it being understood that the terms "alkyl", "alkoxy" and "acyl" denote linear or branched groups containing from 1 to 6 carbon atoms.

Among the pharmaceutically acceptable bases which can be employed for forming salts of the compounds employed according to the invention there may be mentioned, by way of example and without any limitation being implied, sodium hydroxide, potassium hydroxide, triethylamine, diethylamine, ethanolamine, arginine, lysine and diethanolamine.

The invention also relates to the process for the preparation of the compounds of formula (I), in which condensation is carried out, in the presence of a base such as an alkali metal amide or its combination with an alkali metal alcoholate (complex base) and preferably the NaNH2-t-BuONa complex base, of the compound of formula (II):

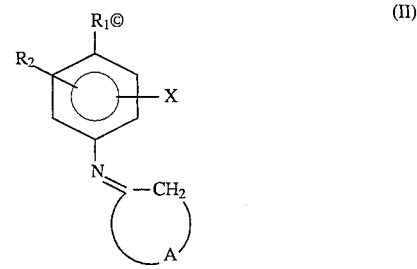

in which R$_2$ and A are as defined in formula (I), R$_1$' is chosen from —O—R$_4$ and —S—R$_5$ with R$_4$ and R$_5$ as defined in formula (I) and X denotes a halogen atom, to obtain:
either a compound of formula (III):

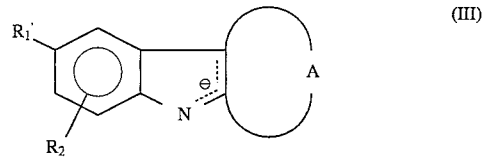

in which R$_2$, A and R$_1$' are as defined above,
or, after hydrolysis, a compound of formula (I$_a$):

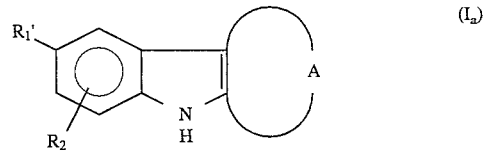

in which R$_2$, A and R$_1$' are as defined above,
a compound of formula (III), or an alkali salt of a compound of formula (I$_a$) which is substituted by a radical of formula R$_3$' on the indole nitrogen, with R$_3$' having the same meaning as R$_3$ as defined in formula (I) with the exception of hydrogen, in order to obtain a compound of formula (I$_a$'):

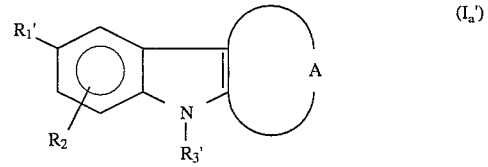

in which R$_2$, A, R$_1$' and R$_3$' are as defined above,
compounds of formula (I$_a$) or (I$_a$') which are, if need be,
either subjected to a dealkylation reaction in order to obtain a compound of formula (I$_b$):

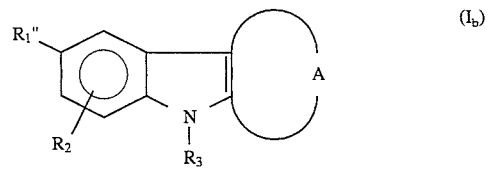

with R$_2$, R$_3$ and A as defined above and R$_1$" denoting a hydroxyl or thiol group,
or subjected to the action of a mixture of formula (IV):

in which X' denotes a halogen and R$_5$' denotes an alkyl, a phenyl or a benzyl,
to obtain, depending on the conditions of use of the compound of formula (IV):
a compound of formula ($I_b$) as defined above,
or a compound of formula ($I_c$):

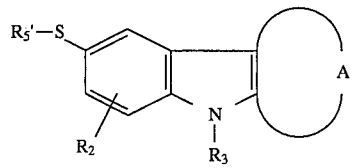
($I_c$)

in which $R_2$, $R_3$, $R_5'$ and A are as defined above,
a compound of formula ($I_c$) which can be subjected to a hydrogenation to obtain the compound of formula ($I_d$):

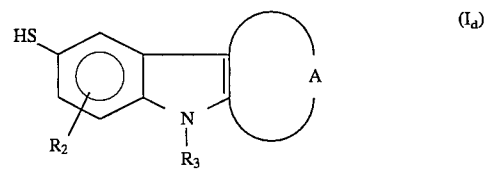
($I_d$)

in which $R_2$, $R_3$ and A are as defined above,
it being understood that the terms "alkyl", "alkoxy" and "acyl" denote linear or branched groups containing 1 to 6 carbon atoms,
the compounds of formulae ($I_a$), ($I_a'$), ($I_b$), ($I_c$) and ($I_d$) forming the group of the compounds of formula (I),
it being possible for the compounds of formula (I) to be, if appropriate:

purified according to one or more methods chosen from crystallization, chromatography on a silica column, extraction, filtration and passing over charcoal or resin, separated, in pure form or in mixed form, into their possible optical isomers, and converted into a salt with a pharmaceutically acceptable base.

The substitution of the compound of formula ($I_a$) or of an alkali salt of a compound of formula ($I_a'$), as defined above, by a radical of formula —$R_3'$, envisaged in the above synthesis process, can be carried out by reaction of a compound of formula ($I_a$) or ($I_a'$) with a compound of formula $R_3'$—X", Cl—COO—$R_3''$, ($R_3'$—O)$_2$SO$_2$, X"—(CH$_2$)$_n$—COOR$_3''$, or ($R_3''$—O—CO)$_2$O in which $R_3'$ is as defined above, $R_3''$ is a ($C_1$-$C_6$)alkyl, n is 1 to 6 and X" denotes a halogen, the reaction being optionally followed by a hydrolysis stage to obtain the acid functional group from the ester in the case where $R_3'$ denotes an alkoxycarbonylalkyl.

For Example the Invention Relates To the preparation of the complex base:

2 equivalents (eq.) of 2-methyl-2-propanol are added dropwise at ambient temperature to a suspension of 7 eq. of NaNH$_2$ (including 2 eq. for the preparation of the alcoholate and 1 eq. for the preparation of the imine enolate or of enamine) in tetrahydrofuran (THF) (7 cm$^3$ for 70 mmol of NaNH$_2$). After this addition the mixture is heated to 45° C. for 2 hours (the NaNH$_2$/t-BuONa ratio is then 2/1 during the cyclization stage).

the cyclization of the imines:

1 eq. of the imine to be condensed in solution in THF (3 cm$^3$ for 1 mmol) is added at 0° C. to the basic medium prepared above. The mixture is stirred magnetically at ambient temperature or 40°–45° C. The reaction is followed by gas phase chromatography.

the preparation of the nitrogen-unsubstituted indoles (hydrolysis):

When all the starting material has disappeared, a hydrolysis carried out at 0° C. After an extraction with ether the organic phase is dried over MgSO$_4$ and the solvents are evaporated off at reduced pressure. The (thia)cycloalkyl[b]indole is then isolated by liquid phase chromatography.

N-methylation in situ: preparation of N-methylated thiacycloalkyl[b]indoles:

When all the starting material has disappeared the reaction mixture is decanted and the liquid part is then transferred to a Mariotte funnel and then added dropwise to 3 eq. of Me$_2$SO$_4$ in solution in THF at 0° C. When the addition is finished the reaction mixture is allowed to return to ambient temperature. After 2 hours the mixture is hydrolysed with a 32% aqueous solution of NH$_4$OH and then extracted with methylene chloride. The organic phase is then dried over MgSO$_4$ and the solvents are evaporated off at reduced pressure. The N-methylated (thia)cycloalkyl[b]indole is then isolated by liquid phase chromatography.

N-carbethoxymethylation in situ: preparation of N-carbethoxymethylated thiacycloalkyl[b]indoles:

The liquid part of the reaction mixture is transferred to a dropping funnel and added dropwise to a solution of BrCH$_2$COOEt (3 eq.) in dimethylformamide (DMF) (6 cm$^3$ for 1 mmol at ambient temperature). After 2 hours, an extraction with ether is carried out and the organic phase is washed with water and then dried over MgSO$_4$ and the solvents are evaporated off at reduced pressure. The thiacycloalkyl[b]indole thus obtained is then isolated by liquid phase chromatography.

saponification: formation of N-(carboxymethyl) thiacycloalkyl[b]indoles:

The N-(carbethoxymethyl)thiacycloalkyl[b]indole prepared above is placed at reflux in a 10% solution of KOH in ethanol. The reaction is followed by thin layer chromatography (TLC).

When all the starting material has disappeared the reaction is thrown onto ice and extracted with ether. The aqueous phase is then acidified and extracted with ether again. The organic phase is dried over MgSO$_4$ and the solvents are then evaporated off at reduced pressure. N-(carboxymethyl)thiacycloalkyl[b]indole is purified by liquid phase chromatography.

The compounds of formula (II) are easily accessible to a person skilled in the art by reaction of an aniline of formula (IIa):

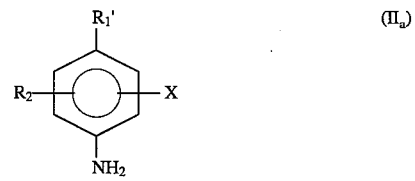
(II$_a$)

in which $R_1'$ and $R_2$ are as defined above,
with a ketone of formula (V):

(V)

in which A is as described in formula (I).

Synthesis of Imines and Enamines

More particularly, imines can be prepared by subjecting 1 eq. of haloamine and 1 eq. of ketone to an azeotropic distillation in benzene (depending on the circumstances the reaction may be catalysed with an acid (APTS, $ZnCl_2$, $ZnBr_2$, $BF_3$-$Et_2O$)). After the sufficient quantity of water has been collected the imine is distilled at reduced pressure.

The raw materials employed during the preparative processes described above are either commercial or easily accessible to a person skilled in the art according to the literature.

The compounds of the present invention have very marked antioxidant properties. Pharmacological studies have shown in particular that these compounds are endowed with remarkable and specific protective activities with regard to lipid peroxidations and especially peroxidations of low-density lipoproteins (LDL).

The compounds of the invention therefore exhibit a particularly novel and beneficial effect in ailments involving a peroxidation phenomenon, especially a lipid peroxidation. These new compounds can be employed in the treatment or the prevention of ailments due or related to such peroxidation phenomena and especially cerebral, renal or cardiac ischemic disorders, atherosclerosis, hemolytic anemias, damage due to the reperfusion process and inflammatory syndromes.

As a result of their effect, the compounds of the invention are also new clinical candidates for the treatment and the prevention of inflammatory diseases and of pathological inflammatory conditions.

The compounds of the invention are, in fact, powerful inhibitors of lipoxygenase (pharmacological study: Example A) and exhibit an intense antiinflammatory activity (pharmacological study: Example B).

The compounds of the invention are consequently useful in the treatment and the prevention of chronic or acute articular, pulmonary, cutaneous or renal inflammation and especially in the prevention and treatment of arthritis, of rheumatoid polyarthritis, osteoarthritis, psoriasis, allergic diseases, asthma, inflammatory diseases of the intestine, gastrointestinal ulcers, ischemia, atherosclerosis, respiratory distress and septic shock.

The compounds of the invention are therefore very powerful antioxidants and also have a strong antiinflammatory activity. It is found that the compounds of the invention also show an antiaggregating activity (test for inhibition of the aggregation induced by arachidonic acid; Bertele et al., Science, 1983, 220: pp. 517–519), a hypolypemiant activity (measurement of hypocholesterolemia: Day et al., Atherosclerosis Drug Discovery, ed. Charles E. Day, Plenum Publishing Corp. New York, 1976, pp. 231–249; Holub et al., Clin. Chem., 1972, 18, pp. 239–243; Aliain et al., Clin. Chem., 1974, 20 (4), pp. 470–475) and a bronchorelaxant activity (test for tracheal relaxation in vitro, Ludvena et al., Arch. Int. Pharmacodyn., 1957, 111, pp. 392–400).

Another subject of the present invention is the pharmaceutical compositions containing a compound of formula (I) or one of its salts of addition to a pharmaceutically acceptable base, in combination with one or a number of pharmaceutically acceptable excipients.

Among the pharmaceutical compositions according to the invention it will be possible to mention more particularly those which are suitable for oral, percutaneous, cutaneous, parenteral, nasal, rectal, perlingual, ocular or pulmonary administration and especially injectable or drinkable preparations, aerosols, eye or nose drops, simple, film-coated or sugar-coated tablets, gelatin tablets, capsules, creams, ointments, skin gels, pills, packets, sachets, granules and suppositories.

The posology varies depending on the patient's age, weight and sex, the route of administration, the nature and the severity of the ailment and depending on any treatments which may be associated. The dosages range between 0.5 mg and 2 g per day, particularly between 0.5 mg and 100 mg per day, for example between 10 mg and 100 mg per day.

The examples which follow illustrate the invention but do not limit it in any way.

Preparation 1

N-cycloheptylidenyl-3-chloro-4-methoxyaniline

The title compound is obtained by azeotropic distillation from 3-chloro-4-methoxyaniline and cycloheptanone, using paratoluenesulfonic acid as catalyst and benzene as solvent.

The reaction is followed by gas phase chromatography. After the reaction has been completed the mixture is returned to ambient temperature, treated with a saturated solution of $NaHCO_3$, extracted with ether and dried over magnesium sulfate. The solvents are removed under vacuum.

The imine is purified by distillation or employed as it is.

Preparation 2

N-cyclooctylidenyl-3-chloro-4-methoxyaniline

The title compound is obtained by proceeding as in preparation 1 but employing cyclooctanone instead of cycloheptanone.

Preparation 3

N-(thiopyraniliden-3-yl)-3-chloro-4-methoxyaniline 1 eq. of 3-chloro-para-anisidine and 1 eq. of thiopyran-3-one are subjected to an azeotropic distillation in benzene (100 cm³ for 50 mmol). The reaction is followed by gas chromatography and stopped after 5 h. The imine is purified by distillation and is obtained in a 40% yield.

$^1$H NMR: 6.3–7.0 (3H, m, arom. H); 3.7 (3H, s, OMe); 3.3 (1H, s, C-H); 3.1 (1H, s, C—H); 2.0–3.0 (m, 6H, 3×$CH_2$)
Mass: 255

EXAMPLE 1

3-hydroxy-10-methyl-5,6,7,8,9,10-hexahydrocyclohept[b]indole

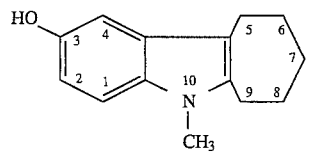

EXAMPLE 1

Stage A:
3-methoxy-5,6,7,8,9,10-hexahydrocyclohept[b]indole

Preparation of the complex base:

2 equivalents (abbreviated to eq. hereinafter) of 2-methyl-2-propanol are added dropwise at ambient temperature to a suspension of 7 equivalents of $NaNH_2$ in tetrahydrofuran (THF) (7 cm³ for 70 mmol of $NaNH_2$). After this addition the mixture is heated to 45° C. for 2 h.

Condensation:

1 eq. of N-cycloheptylidenyl-3-chloro-4-methoxy-aniline is added a, 0° C. to the complex base prepared above. The mixture is stirred at ambient temperature until the reaction has been completed. The reaction is followed by gas chromatography. 3-Methoxy-5,6,7,8,9,10-hexahydrocyclohept[b]indole is isolated by liquid phase chromatography.

Stage B:
3-methoxy-10-methyl-5,6,7,8,9,10-hexahydrocyclohept[b]indole

After decantation, the liquid obtained above is transferred into a solution of 3 eq. of dimethylsulfate, with stirring, at 0° C. The reaction mixture is then stirred for 1 h at ambient temperature. The mixture is poured onto ice, extracted with ether and washed with a 32% solution of ammonium hydroxide. The expected compound is purified by liquid phase chromatography.

Yield: 53%

2nd process:

The indole derivative obtained in the preceding stage, in solution in dimethylformamide (DMF), is added dropwise at 0° C. to a suspension of 2 eq. of sodium hydride in DMF (10 $cm^3$ of DMF for 1 mmol of indole substrate).

The reaction mixture is allowed to return to ambient temperature and 3 eq. of dimethyl sulfate are then added.

The mixture is then treated in the same way as in the first process above.

Stage C:
3-hydroxy-10-methyl-5,6,7,8,9,10-hexahydrocyclohept[b]indole 1 eq. of the compound obtained in the preceding stage, diluted in methylene chloride (5 $cm^3$ for 3 mmol), is added dropwise at 0° C. to a mixture consisting of 1.5 eq. of $AlCl_3$ and 20 eq. of $CH_3CH_2$—SH.

Yield: 60–91%

Melting point: 102° C.

Microanalysis:

|  | C % | H % | N % |
| --- | --- | --- | --- |
| Calculé (calc.) | 78.10 | 7.96 | 6.50 |
| Trouvé (Tr.) | 77.59 | 7.85 | 6.52 |

Spectrum characteristics:

IR (cm-1): 3349 (OH); 2920–2845 (aliphatic).

1H NMR (CDCl3) δ ppm: 6.5–7.3 (m, 3H, aromatic H); 5.2 (s, 1H, OH exchanged with $D_2O$); 3.6 (s, 3H, $NCH_3$); 2.5–3.0 (m, 4H, $2\times CH_2$); 1.5–2.0 (m, 6H, $3\times CH_2$).

EXAMPLE 2

3-Methoxy-10-Methyl-5,6,7,8,9,10,11-Heptahydrocyclooct[b]indole

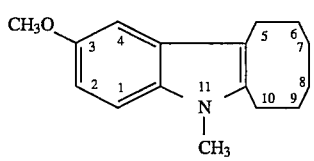

EXAMPLE 1

The title compound is obtained by proceeding as in Stages A and B of Example 1 but replacing N-cyclo-heptylidenyl-3-chloro-4-methoxyaniline in Stage A with N-cyclooctylidenyl-3-chloro-4-methoxyaniline.

Yield: 60%

Melting point (petroleum ether+ethanol): 54° C.

Microanalysis:

|  | C % | H % | N % |
| --- | --- | --- | --- |
| Calculé | 78.96 | 8.69 | 5.75 |
| Trouvé | 78.90 | 8.52 | 5.82 |

Spectrum characteristics:

IR (cm-1): 2921–2848 (aliphatic).

1H NMR (CDCl$_3$) δ ppm: 7.10–6.50 (m, 3H, aromatic H); 3.78 (s, 3H, $OCH_3$); 3.68 (s, 3H, $NCH_3$); 3.00–2.60 (m, 4H, $2\times CH_2$); 1.90–1.20 (m, 8H, $4\times CH_2$).

EXAMPLE 3

3-ethylthio-10-methyl-5,6,7,8,9,10-hexahydrocyclohept[b]indole 500 mg (1.9 mmol) of the compound obtained in Stage B of Example 1, predissolved in 5 $cm^3$ of methylene chloride distilled over phosphorus pentoxide are added dropwise to a mixture, cooled to 0° C., of 380 mg (2.84 mmol) of aluminum chloride and 2.3 g (37.9 mmol) of ethanethiol. After stirring for 1 h at 0° C., 1.5 eq. of aluminum chloride and 20 eq. of ethanethiol are added again. The mixture is stirred again for 1 h at 0° C. and then poured onto ice, treated with 1N hydrochloric acid and then extracted with dichloromethane. After treatment of the organic phase and purification of the crude product by chromatography on a silica column, the expected compound is obtained.

Yield: 55%

Melting point: 44° C.

|  | C % | H % | N % | S % |
| --- | --- | --- | --- | --- |
| Calculé | 74.07 | 8.16 | 5.39 | 12.36 |
| Trouvé | 74.04 | 8.16 | 5.36 | 12.40 |

IR (cm-1): 2921–2846 (aliphatic)

1H NMR (CDCl$_3$) δ ppm: 7.60 (s, 1H, aromatic H); 7.25–7.10 (m, 2H, aromatic H); 3.60 (s, 3H, $NCH_3$); 2.90–2.70 (q+m, 6H, $SCH_2+2\times CH_2$); 1.95–1.70 (m, 6H, $3\times CH_2$); 1.30–1.15 (t, 3H, $CH_3$). 13C NMR (CDCl$_3$) δ ppm: 139.86 (C5); 135.17 (C1); 128.25 (C3); 125.16 (C4);'123.77 (C8); 122.37 (C6); 111.32 (C2); 109.10 (C7); 31.46–30.81 (C9); 29.55 (C16) 28.31–26.93–26.25–24.22 (C11, 12, 13, 14, 15); 14.80 (C10).

EXAMPLE 4

Ethyl 2-[3-methoxy-5,6,7,8,9,10-hexahydrocyclohept[b]indol-10-yl]acetate

The title compound is obtained by proceeding as in Example 1 in Stages A and B but using ethyl bromoacetate in Stage B instead of dimethylsulfate.

EXAMPLE 5

2-[3-methoxy-5,6,7,8,9,10-hexahydrocyclohept[b]indol-10 yl]acetic acid

The title compound is obtained by carrying out the hydrolysis of the ester functional group of the compound obtained in Example 4.

EXAMPLE 6

10-methyl-3-phenylthio-5,6,7,8,9,10-hexahydrocyclohept[b]indole

The title compound is obtained by proceeding as in Example 3 but replacing ethanethiol ($CH_3CH_2$—SH) in Stage C with thiophenol ($C_6H_5$-SH).

EXAMPLES 7 TO 21

The compounds of the examples set out in Table (I) which follows can be obtained by following the methods described in the preceding examples and by employing the appropriate reactants:

STAGE A:

Preparation of the complex base:

2 eq. of 2-methyl-2-propanol are added dropwise at ambient temperature to a suspension of 7 eq. of $NaNH_2$ in tetrahydrofuran (7 cm$^3$ for 70 mmol of $NaNH_2$). After this addition the mixture is heated to 45° C. for 2 hours.

STAGE B:

Condensation:

Procedure 1:

1 eq. of N-(thiopyranyliden-3-yl)-3-chloro-4-methoxyaniline (preparation 3) in solution in THF (30 cm$^3$ for 10 mmol) is added at 0° C. to the complex base prepared above.

The mixture is stirred at ambient temperature for 12 h. The reaction is followed by gas chromatography. At the end of reaction the reaction mixture is thrown onto ice and extracted with ether.

After drying over MgSO4 and evaporation of the solvents at reduced pressure the title compound is isolated by flash chromatography (Kieselgel 40–63μ) with a 5% ethyl acetate/petroleum ether eluent.

Yield: 53% based on the imine.

TABLE (I)

(I)

| N° Exemple | $R_1$ | $R_2$ | $R_3$ | n |
|---|---|---|---|---|
| 7 | —S—$CH_3$ | H | —$CH_3$ | 1 |
| 8 | —O—$CH_3$ | H | —$CH_2$—$CH_3$ | 1 |
| 9 | —O—$CH_3$ | H | —$CH_2$—$CH_2$—$CH_3$ | 1 |
| 10 | —O—$CH_3$ | H | —CO—$CH_3$ | 1 |
| 11 | —O—$CH_3$ | H | —$(CH_2)_3$—$CH_3$ | 1 |
| 12 | —O—$CH_3$ | —O—$CH_3$ | —$CH_3$ | 1 |
| 13 | —OH | H | —$CH_2$—$CH_3$ | 1 |
| 14 | —OH | H | —$CH_2$—$CH_2$—COO—$CH_2$—$CH_3$ | 1 |
| 15 | —OH | H | —$CH_2$—$CH_2$—COOH | 1 |
| 16 | —OH | H | —$CH_3$ | 2 |
| 17 | —S—$CH_2$—$CH_3$ | H | —$CH_3$ | 2 |
| 18 | —O—$CH_3$ | H | —$CH_2$—$CH_2$—COO—$CH_2$—$CH_3$ | 2 |
| 19 | —O—$CH_3$ | H | —$CH_2$—$CH_2$—COOH | 2 |
| 20 | —S—$CH_2$—$C_6H_5$ | H | —$CH_3$ | 1 |
| 21 | —SH | H | —$CH_3$ | 1 |

Physico-chemical data:

Melting point of Example 16: 98° C.

Synthesis of thiopyrano[3,2-b]indoles by cyclization of imines followed by hydrolysis:

The synthesis of indole is described for the compound of Example 22:

EXAMPLE 22

8-methoxythiopyrano[3,2b]indole

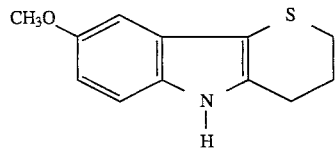

Example 22

Melting point (Totoli): 123° C.

IR: 3390 (NH), 2999, 2938, 2922, 2834 (C—H)

| Analysis ($C_{12}H_{13}ONS$): | Calc.: C | 65.72 | H | 5.97 | N | 6.38 | S | 14.62 |
|---|---|---|---|---|---|---|---|---|
| | F.: | 65.95 | | 6.03 | | 6.53 | | 14.93 |

Procedure 2:

The crude imine prepared during preparation 3 from 1 eq. of ketone+ 1 eq. of amine is added at 0° C., without purification, to the complex base prepared above. The reaction is performed as in procedure 1.

Yield: 36.5% based on the ketone.

Synthesis of N-carbethoxymethylated indoles:

The synthesis will be described for the compound of Example 23:

EXAMPLE 23

Ethyl 2-(8-methoxythiopyrano[3,2-b]indol-5-yl)acetate

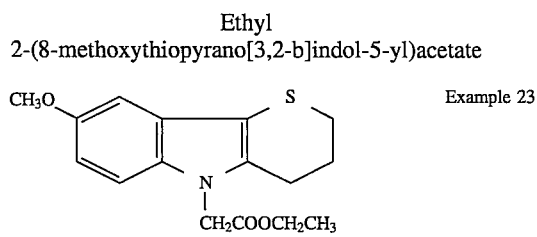

Example 23

At the end of the reaction performed in Example 22 (procedure 1 or 2), the reaction mixture is left settled under a nitrogen stream. The supernatant is transferred at ambient temperature to a solution of 4 eq. of $BrCH_2COOCH_2CH_3$ in dimethylformamide (DMF) (so as to have a THF/DMF= ½ mixture at the end of the addition). When the reaction is finished (followed by thin layer chromatography (TLC)), the reaction mixture is thrown onto ice and extracted with ether. After drying over $MgSO_4$ and evaporation of the solvents, the title compound is isolated by flash chromatography with a 15% acetone/hexane eluent.

Yield: 46% based on the imine

Melting point (Totoil): 98° C.

IR: 2923 (C—H); 1750 (C=O)

| Analysis ($C_{16}H_{19}O_3NS$): | Calc.: C | 62.92 | H | 6.27 | N | 4.58 | S | 10.49 |
|---|---|---|---|---|---|---|---|---|
| | F.: | 62.58 | | 6.32 | | 4.69 | | 10.36 |

EXAMPLE 24

8-methoxy-5-methylthiopyrano[3,2-b]indole

The compound obtained in Example 22 is subjected to the action of 3 eq. of dimethyl sulfate, with stirring, at 0° C. The reaction mixture is then stirred for 1 h at ambient temperature. The mixture is poured onto ice, washed with a 32% solution of ammonium hydroxide and then extracted with ether. The expected compound is purified by liquid phase chromatography.

Yield: 53%

2nd process:

The compound obtained in Example 22, in solution in dimethylformamide (DMF) is added dropwise, at 0° C., to a suspension of 2 eq. of sodium hydride in DMF (10 cm³ of DMF for 1 mmol of indole substrate). The reaction mixture is allowed to return to ambient temperature and 3 eq. of dimethyl sulfate are then added. The mixture is then treated in the same way as in the first process above.

EXAMPLE 25

8-hydroxy-5-methylthiopyrano[3,2-b]indole

The compound of Example 25 is obtained by demethylation of the compound obtained in Example 24.

EXAMPLE 26

8-Ethylthio-5-methylthiopyrano[3,2-b]indole 500 mg (1.9 mmol) of the compound obtained in Example 24, predissolved in 5 cm³ of methylene chloride distilled over phosphorus pentoxide are added dropwise to a mixture, cooled to 0° C., of 380 mg (2.84 mmol) of aluminum chloride and 2.3 g (37.9 mmol) of ethanethiol. After stirring at 0° C. for 1 h, 1.5 eq. of aluminum chloride and 20 eq. of ethanethiol are added again. The mixture is stirred again for 1 h at 0° C. and then poured onto ice, treated with 1N hydrochloric acid and then extracted with dichloromethane. After treatment of the organic phase and purification of the crude product by chromatography on a silica column the expected compound is obtained.

EXAMPLE 27

2-(8-methoxythiopyrano[3,2-b]indol-5-yl)acetic acid

The title compound is obtained by carrying out the hydrolysis of the ester functional group of the compound obtained in Example 23.

EXAMPLE 28

5-methyl-8-benzylthiothiopyrano[3,2-b]indole

The title compound is obtained by proceeding as in Example 26 but replacing ethanethiol ($CH_3CH_2SH$) with benzylthiol ($C_6H_5$—$CH_2$—SH).

EXAMPLES 27 TO 36

The compounds set out in Table (II) which follows can be obtained by following the methods described in the preceding examples and by employing the appropriate reactants:

TABLEAU (II)

$$\text{(II)}$$

Structure: bicyclic indole with $R_1$, $R_2$ on benzene ring, $R_3$ on N, and S–$(CH_2)_p$ side chain.

| N° Exemple | $R_1$ | $R_2$ | $R_3$ | p |
|---|---|---|---|---|
| 27 | —OH | —H | —H | 2 |
| 28 | —O—$CH_3$ | —H | —$CH_2$—$CH_3$ | 2 |
| 29 | —O—$CH_3$ | —H | —$CH_2$—$CH_2$—$CH_3$ | 2 |
| 30 | —O—$CH_3$ | —H | —$(CH_2)_3$—$CH_3$ | 2 |
| 31 | —O—$CH_3$ | —$OCH_3$ | —$CH_3$ | 2 |
| 32 | —OH | —H | —$CH_2$—$CH_3$ | 2 |
| 33 | —OH | —H | —$CH_2$—$CH_2$—COO—$CH_2$—$CH_3$ | 2 |
| 34 | —OH | —H | —$CH_2$—$CH_2$—COOH | 2 |
| 35 | —O—$CH_3$ | —H | —CH($CH_3$)$_2$ | 2 |
| 36 | —O—$CH_3$ | —H | —$CH_2$COO—CH($CH_3$)$_3$ | 2 |
| 37 | —OH | —H | —$CH_2$COO—$CH_2CH_3$ | 2 |
| 38 | —OH | —H | —$CH_2$—COOH | 2 |

EXAMPLE 39

Ethyl 2-[3-hydroxy-5,6,7,8,9,10,11-heptahydrocyclooct[b]indol-11-yl]acetate

Melting point: 100° C.

EXAMPLE 40

2-[3-hydroxy-5,6,7,8,9,10,11-heptahydrocyclooct[b]indol-11 yl]acetic acid

EXAMPLE 41

3-methoxy-5,6,7,8,9,10,11-heptahydro-cyclooct[b]indole

EXAMPLE 42

Ethyl 2-[3-methoxy-5,6,7,8,9,10,11-heptahydrocyclooct[b]indol-11-yl]acetate

EXAMPLE 43

Tert-butyl 2-[3-methoxy-5,6,7,8,9,10,11-heptahydrocyclooct[b]indol-11-yl]acetate

PHARMACOLOGICAL STUDY

EXAMPLE A

Study of the Protective Power for the Oxidation of the LDLs

The ability of the compounds of the invention to decrease the oxidized proportions of LDL was measured as follows: a 24 h incubation is carried out combining natural LDLs (Low Density Lipoproteins), a $Cu^{2+}$ free-radical generating system and the compounds to be tested.

The results are obtained after analysis of the mixture by a high performance chromatography technique: FPLC (Fast Protein Liquid Chromatography). The protective power of the test compound is determined after comparison of the chromatogram obtained with that of the positive reference control, probucol. It is clearly seen that the compounds of the invention have a very great protective power. By way of comparison, at a concentration of $10^{-5}$M, the degree of protection obtained for the compounds of the invention exceeds that of probucol. This is the case especially with the compound of Example 1, which permits a very strong protection against a system which oxidizes the LDLs (75% of unoxidized form at $10^{-5}$M).

EXAMPLE B

Study of the Antiperoxidizing Activity

The action of the compounds employed according to the invention which are capable of trapping the HO• radicals was studied, on the one hand, in the spontaneous peroxidation of lipids and, on the other hand, in the peroxidation induced by the $Fe^{2+}$-ascorbate system (10 μM–250 μM), this being done on rat brain homogenates.

a) Study of spontaneous lipid peroxidation

During the measurement of spontaneous lipid peroxidation rat brain homogenates are placed in the presence or in the absence of the compounds to be tested for 60 min at 37° C. The reaction is stopped at 0° C. and the quantitative determination of malonodialdehyde is performed with the aid of thiobarbituric acid. Lipid peroxidation is determined by the substances reacting with thiobarbituric acid, expressed in nanomoles of malonodialdehyde.

b) Study of induced lipid peroxidation

During the measurement of induced lipid peroxidation the methodology is identical with that described above except for the addition of the $Fe^{2+}$-ascorbate radical-inducing system to the homogenate. The reference substances are probucol and vitamin E. The concentrations of the test compounds inhibiting the peroxidation of the substrate by 50% ($IC_{50}$) are calculated.

It has been seen that the compounds of formula (I), employed according to the invention, have a particularly intense antiperoxidizing activity, since they have a clearly greater antiperoxidizing activity than probucol and vitamin E, which is the natural antioxidant of the human organism.

For example, the compound of Example 1 exhibits an $IC_{50}$ lower than $10^{-7}M$.

EXAMPLES C AND D

The compounds of the invention are also tested in 2 tests enabling an antioxidant activity to be detected.

EXAMPLE C

Inhibition of the Formation of Conjugated Dienes

1 $cm^3$ of linoleic acid emulsion is incubated for 30 min at 37° C. in the presence of a solution of $FeSO_4$ (final concentration 4 µmol/l) with and without the compound to be tested (final volume 1.55 $cm^3$).

The dienes are extracted with 8 $cm^3$ of chloroform/methanol (2/1) mixture.

After centrifuging, 2 $cm^3$ of the underlying organic phase are removed and stirred for 10 min with an aqueous solution at pH 2.

After centrifuging, 0.250 $cm^3$ of the organic phase are removed and evaporated under nitrogen.

2 $cm^3$ of hexane are then added and the optical density (OD) is measured at 233 nm.

Each quantitative determination is carried out in triplicate. 4 to 5 h are needed to carry out a manipulation including 6 determinations (including blank and Fe reference).

The percentage inhibition of the formation of conjugated dienes is calculated by comparison with 100% of dienes formed with the $Fe^{2+}$ control.

The compounds of the invention are found to be very efficient in the inhibition of the formation of dienes, which confirms their antioxidant nature.

For example, the compound of Example 1, in a concentration of $10^{-5}M$, inhibits the formation of dienes by 92%.

EXAMPLE D

Protection of Red Blood Corpuscles Against Hemolysis Induced by AAPH

After centrifuging a sample of human blood the red blood corpuscles are washed three times with 0.9% NaCl and 0.250 $cm^3$ of residue is suspended in 50 $cm^3$ of 0.9% NaCl.

75 mM of AAPH in a volume of 0.750 $cm^3$ are placed in contact with 1 $cm^3$ of suspension of red blood corpuscles and $10^{-5}M$ of the product to be tested in a volume of 0.200 $cm^3$. An AAPH-free control is carried out simultaneously for each test product, as well as a red blood corpuscle control and an AAPH control without test product.

After 30 min of incubation with stirring on a water bath at 37° C. the suspension of red blood corpuscles is centrifuged for 10 min at +4° C. (3000 rev/min) and the optical density at 403 nm of the supernatant is measured in comparison with the AAPH-free control.

The percentage inhibition of hemolysis is calculated by comparison with 100% of hemolysis obtained with the AAPH control.

The compounds of the invention protect the red blood corpuscles against hemolysis in a highly significant manner.

For example, at $10^{-5}M$, the compound of Example 1 inhibits hemolysis by 74%.

EXAMPLE E

Pharmaceutical Composition: Tablets

Preparation formula for 1000 tablets containing a 50 mg dose.

| | |
|---|---|
| 8-Methoxythiopyrano[3,2-b]indole | 50 g |
| Wheat starch | 15 g |
| Corn starch | 15 g |
| Lactose | 65 g |
| Magnesium stearate | 2 g |
| Silica | 1 g |
| Hydroxypropyl cellulose | 2 g |

EXAMPLE F

Pharmaceutical Composition: Tablets

Preparation formula for 1000 tablets containing a 50 mg dose.

| | |
|---|---|
| 3-Hydroxy-10-methyl-5,6,7,8,9,10-hexahydro-cyclohept[b]indole | 50 g |
| Wheat starch | 15 g |
| Corn starch | 15 g |
| Lactose | 65 g |
| Magnesium stearate | 2 g |
| Silica | 1 g |
| Hydroxypropyl cellulose | 2 g |

We claim:
1. A compound selected from those of formula (I):

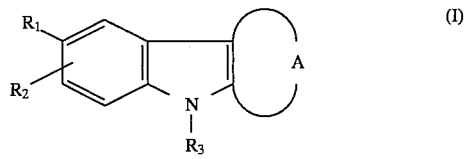

in which:

A denotes an alkylene chain —$(CH_2)_m$— with m denoting 5 or 6 or a group of formula (a)

in which p is 1 to 4, inclusive $R_1$ denotes a radical chosen from:
hydroxyl,
thiol,
—O—$R_4$ with $R_4$ being chosen from alkyl and acyl;
and —S—$R_5$ with $R_5$ being chosen from alkyl, phenyl and benzyl;

$R_2$ denotes a radical chosen from hydrogen, halogen, alkyl, alkoxy and trifluoromethyl;

$R_3$ denotes a radical chosen from acyl, carboxyalkyl and alkoxycarbonylalkyl; and, in the case where A is other than $(CH_2)_m$— also hydrogen oralkyl;

its optical isomers, in pure form or in mixed form, when $R_1$, $R_2$ or $R_3$ have a chiral center, and its addition salts with a pharmaceutically-acceptable base, it being understood that the terms "alkyl", "alkoxy" and "acyl" denote linear or branched groups containing 1 to 6 carbon atoms, inclusive.

2. A compound as claimed in claim 1 selected from those, wherein A denotes a pentamethylene chain, its optical isomers in pure form or in mixed form, and its addition salts with a pharmaceutically-acceptable base.

3. A compound as claimed in claim 1 selected from those wherein A denotes a pentamethylene chain and $R_1$ denotes hydroxyl, its optical isomers in pure form or in mixed form, and its addition salts with a pharmaceutically-acceptable base.

4. The compound as claimed in claim 1, which is 8-methoxythiopyrano [3,2-b]indole.

5. The compound as claimed in claim 1, which is ethyl 2-(8-methoxythiopyrano[ 3,2-b]indol-5-yl)acetate.

6. A pharmaceutical composition containing an antiperoxidation amount of a compound of claim 1, in combination with a pharmaceutically-acceptable excipient.

7. A method of treating a mammal which is affected with a peroxidation phenomenon, comprising the step of administering to the said mammal an amount of a compound selected from those of formula (I):

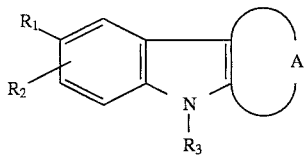
(I)

in which:

A denotes an alkylene chain —$(CH_2)m$— with m denoting 5 or 6 or a group of formula (a)

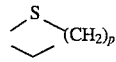
(a)

in which p is 1 to 4, inclusive, $R_1$ denotes a radical chosen from:
hydroxyl,
thiol,
—O—$R_4$ with $R_4$ being chosen from alkyl and acyl;
and —S—$R_5$ with $R_5$ being chosen from alkyl, phenyl and benzyl;

$R_2$ denotes a radical chosen from hydrogen, halogen, alkyl, alkoxy and trifluoromethyl;

$R_3$ denotes a radical chosen from hydrogen, alkyl, acyl, carboxyalkyl, and alkoxycarbonylalkyl;

its optical isomers, in pure form or in mixed form, when $R_1$, $R_2$, or $R_3$ have a chiral center, and its addition salts with a pharmaceutically-acceptable base, it being understood that the terms "alkyl", "alkoxy" and "acyl" denote linear or branched groups containing 1 to 6 carbon atoms, inclusive, which is effective for alleviation of the said phenomenon.

8. A method of claim 7 wherein the phenomenon treated is a lipid peroxidation.

9. A method of claim 7 wherein the compound is selected from those, wherein A denotes a pentamethylene chain, its optical isomers in pure form or in mixed form, and its addition salts with a pharmaceutically-acceptable base.

10. A method of claim 7 wherein the compound is selected from those, wherein A denotes a pentamethylene chain and $R_1$ denotes hydroxyl, its optical isomers in pure form or in mixed form, and its addition salts with a pharmaceutically-acceptable base.

11. A method of claim 7 wherein the compound is selected from 3-hydroxy-10-methyl-5,6,7,8,9,10-hexahydrocyclohept[b]indole and an addition salt thereof with a pharmaceutically-acceptable base.

12. A method of claim 7 wherein the compound is 3-methoxy-11-methyl-5,6,7,8,9,10,11-heptahydrocyclooct[b]indole.

13. A method of claim 7 wherein the compound is 8-methoxythiopyrano[ 3,2-b]indole.

14. A method of claim 7 wherein the compound is ethyl 2-(8-methoxythiopyrano[ 3,2-b]indol-5-yl-acetate.

15. A method of claim 7 wherein the compound is in the form of a pharmaceutical composition containing an antiperoxidation amount of the same together with a pharmaceutically-acceptable excipient.

* * * * *

UNITED STATES PATENT AND TRADEMARK OFFICE
CERTIFICATE OF CORRECTION

PATENT NO. : 5,491,163          Page 1 of 5
DATED : Dec. 13, 1995
INVENTOR(S) : Paul Caubere; Brigitte Jamart-Gregoire; Catherine Caubere; Jean-Guy Bizot-Espiard; Pierre Renard; Gerard Adam It is certified that error appears in the above-indentified patent and that said Letters Patent is hereby corrected as shown below:

Title Page, [56] References Cited, U.S. Patent Documents, line 3: "3,329,517" should read -- 3,329,571 --. See Substitute Form PTO 892, Notice of References Cited.

Column 1, line 36: "formula (a)" should read -- formula ($\alpha$) --. Pg 2, line 6

Column 1, line 37: "(a)" should read -- ($\alpha$) --. Pg. 2, line 7

Column 2, line 7: "$R_1^{©}$" should read -- $R_1'$ --. Pg 3, line 4

Column 3, line 51: Add -- : -- to end of line. Pg. 6, line 16

Column 4, line 4: Insert -- is -- before "carried." Pg. 7, line 1

Column 5, line 49: "Aliain" should read -- Allain --. Pg. 9, line 32

Column 7, line 3: "is added a," should read -- is added at --. Pg. 12, line 2

UNITED STATES PATENT AND TRADEMARK OFFICE
CERTIFICATE OF CORRECTION

PATENT NO. : 5,491,163

DATED : Dec. 13, 1995

INVENTOR(S) : Paul Caubere; Brigitte Jamart-Gregoire; Catherine Caubere; Jean-Guy Bizot-Espiard; Pierre Renard; Gerard Adam It is certified that error appears in the above-indentified patent and that said Letters Patent is hereby corrected as shown below:

Column 7, line 6:   Delete "[" at end of the line.
        Pg 12, line 6
    Column 7, line 7:   Add "[" to beginning of the
        line.  Pg. 12, line 7.
    Column 7, line 10:  Delete "[" at the end of line.
        Pg. 12, line 7
    Column 7, line 11:  Add -- [ -- to beginning of
        line.  Pg. 12, line 8.
    Column 7, line 33:  Delete "[" at end of the line.
        Pg. 12, line 25
    Column 7, line 34:  Add -- [ -- to beginning of
        the line.  Pg. 12, line 26
    Column 7, line 59:  Add a -- - -- (dash) to the
        end of line.  Pg. 13, line 8
    Column 7, line 60:  Delete "-" (dash) at
        beginning of the line.  Pg. 13, line 9
    Column 7, line 61:  "EXAMPLE 1" should read
        -- EXAMPLE 2 --.  Pg. 13, line 10

UNITED STATES PATENT AND TRADEMARK OFFICE
CERTIFICATE OF CORRECTION

PATENT NO. : 5,491,163
DATED : Dec. 13, 1995
INVENTOR(S) : Paul Caubere; Brigitte Jamart-Gregoire; Catherine Caubere; Jean-Guy Bizot-Espiard; Pierre Renard; Gerard Adam It is certified that error appears in the above-indentified patent and that said Letters Patent is hereby corrected as shown below:

Column 8, line 24: Delete "[" at end of line. Pg. 14, line 5

Column 8, line 25: Add -- [ -- to beginning of the line. Pg. 14, line 6

Column 9, line 4: "10 yl]" should read -- 10-yl] --. Pg. 15, line 9

Column 9, line 16: "C6H5-SH" should read --($C_6H_5$-SH) --. Pg. 15, line 16

Column 10, line 18: "MgSO4" should read -- $MgSO_4$ --. Pg. 17, line 18

Column 13, line 31: Delete "[" at end of the line. Pg. 21, ln 1

Column 13, line 32: Add -- [ -- to beginning of the line. Pg. 21, line 2

Column 13, line 38: Add a -- - -- (dash) to end of line. Pg. 21, line 4

Column 13, line 39: "yl] acetic acid" should be moved up one line and centered. Pg. 21, ln 5

UNITED STATES PATENT AND TRADEMARK OFFICE
CERTIFICATE OF CORRECTION

PATENT NO. : 5,491,163
DATED : Dec. 13, 1995
INVENTOR(S) : Paul Caubere; Brigitte Jamart-Gregoire; Catherine Caubere; Jean-Guy Bizot-Espiard; Pierre Renard; Gerard Adam It is certified that error appears in the above-indentified patent and that said Letters Patent is hereby corrected as shown below:

Column 13, line 49: Delete "[" at the end
    of the line. Pg. 21, line 7
Column 13, line 50: Add -- [ -- to beginning
    of the line. Pg. 21, line 8
Column 16, line 49: "formula (a)" should read
    -- formula ($\alpha$) --. Pg. 25, line 5
Column 16, line 50: "(a)" should read
    -- ($\alpha$) --. Pg. 25, line 6
Column 16, line 64: "-(CH$_2$)m-" should read
    -- -(CH$_2$)m-, --.
Column 16, line 64: "oralkyl;" should read
    -- or alkyl; --. Pg. 2 of the Response
    and Amendment dtd 6/21/95, <u>Claim 1, line 17.</u>

UNITED STATES PATENT AND TRADEMARK OFFICE
CERTIFICATE OF CORRECTION

PATENT NO. : 5,491,163
DATED : Dec. 13, 1995
INVENTOR(S) : Paul Caubere; Brigitte Jamart-Gregoire; Catherine Caubere; Jean-Guy Bizot-Espiard; Pierre Renard; Gerard Adam It is certified that error appears in the above-indentified patent and that said Letters Patent is hereby corrected as shown below:

Column 17, line 35: "formula (a)" should read -- formula ($\alpha$) --. Pg. 3 of R&A dtd 6/21/95, line 2 of Claim 10.

Column 17, line 37 (approx.): "(a)" should read -- ($\alpha$) --. Pg. 3 of R&A dtd 6/21/95, line 3 of Claim 10.

Signed and Sealed this

Fourteenth Day of May, 1996

Attest:

BRUCE LEHMAN

Attesting Officer    Commissioner of Patents and Trademarks